United States Patent [19]

Benedict et al.

[11] Patent Number: 4,902,679

[45] Date of Patent: Feb. 20, 1990

[54] METHODS OF TREATING DISEASES WITH CERTAIN GEMINAL DIPHOSPHONATES

[75] Inventors: James J. Benedict, Norwich, N.Y.; Christopher M. Perkins, Cincinnati, Ohio

[73] Assignee: Norwich Eaton Pharmaceuticals, Inc., Norwich, N.Y.

[21] Appl. No.: 808,584

[22] Filed: Dec. 13, 1985

[51] Int. Cl.$^4$ ............................................. A61K 31/675
[52] U.S. Cl. ...................................... 514/86; 514/79; 514/89
[58] Field of Search ...................... 514/75, 86, 89, 107, 514/108; 424/128, 57

[56] References Cited

U.S. PATENT DOCUMENTS

| | | | |
|---|---|---|---|
| 4,473,560 | 9/1984 | Biere et al. | 424/202 |
| 4,687,767 | 9/1987 | Bosies et al. | 514/89 |
| 4,687,768 | 9/1987 | Benedict et al. | 514/102 |

FOREIGN PATENT DOCUMENTS 186405  7/1986  European Pat. Off.

*Primary Examiner*—Douglas W. Robinson
*Assistant Examiner*—Richard Kearse
*Attorney, Agent, or Firm*—Milton B. Graff, IV; David L. Suter; Jack D. Schaeffer

[57] ABSTRACT

Methods of treating non-inflammatory diseases characterized by abnormal calcium and phosphate metabolism comprising administering a pharmaceutical composition comprising a geminal diphosphonic acid compound in which the diphosphonic acid-containing carbon is linker via a sulfur atom or a sulfur-containing chain to a 6-membered aromatic ring containing one or more nitrogen atoms.

19 Claims, No Drawings

METHODS OF TREATING DISEASES WITH CERTAIN GEMINAL DIPHOSPHONATES

TECHNICAL FIELD

This invention relates to a method of treating or preventing non-inflammatory diseases characterized by abnormal calcium and phosphate metabolism, in particular those which are characterized by abnormal bone metabolism.

BACKGROUND OF THE INVENTION

A number of non-inflammatory pathological conditions which can afflict warm-blooded animals involve abnormal calcium and phosphate metabolism. Such conditions may be divided into two broad categories.

1. Conditions which are characterized by anomalous mobilization of calcium and phosphate leading to general or specific bone loss or excessively high calcium and phosphate levels in the fluids of the body. Such conditions are sometimes referred to herein as pathological hard tissue demineralizations.

2. Conditions which cause or result from deposition of calcium and phosphate anomalously in the body. These conditions are sometimes referred to herein as pathological calcifications. Many of them result in tissue inflammation, but some do not.

The first category includes osteoporosis, a condition in which bone hard tissue is lost disproportionately to the development of new hard tissue. Marrow and bone spaces become larger, fibrous binding decreases, and compact bone becomes fragile. Osteoporosis can be subclassified as post-menopausal, senile, drug induced (e.g., adrenocorticoid, as can occur in steroid therapy), disease induced (e.g., arthritic and tumor), etc., however, the manifestations are essentially the same. Another condition in the first category is Paget's disease (osteitis deformans). In this disease, dissolution of normal bone occurs which is then haphazardly replaced by soft, poorly mineralized tissue such that the bone becomes deformed from pressures of weight bearing, particularly in the tibia and femur. Hyperparathyroidism, hypercalcemia of malignancy, and osteolytic bone metastases are conditions also included in the first category.

The second category, involving conditions manifested by anomalous calcium and phosphate deposition, includes non-inflammatory afflictions such as myositis ossificans progressiva and calcinosis universalis.

Polyphosphonic acids and their pharmaceutically-acceptable salts have been proposed for use in the treatment and prophylaxis of such conditions. In particular diphosphonates, like ethane-1-hydroxy-1,1-diphosphonic acid (EHDP), propane-3-amino-1-hydroxy-1,1-diphosphonic acid (APD), and dichloromethane diphosphonic acid (Cl$_2$MDP) have been the subject of considerable research efforts in this area. Paget's disease and heterotopic ossification are currently successfully treated with EHDP. The diphosphonates tend to inhibit the resorption of bone tissue, which is beneficial to patients suffering from excessive bone loss. However, EHDP, APD and many other prior art diphosphonates have the propensity of inhibiting bone mineralization when administered at high dosage levels.

It is believed that mineralization inhibition is predominantly a mass related physico-chemical effect, whereas resorption inhibition results from a biological interaction with the cells. It is therefore desirable to develop more biologically potent diphosphate compounds that can be administered at low dosage levels which cause little or no mineralization inhibition, thereby resulting in a wider margin of safety. Low dosage levels are also desirable to avoid the gastro-intestinal discomfort (like diarrhea) sometimes associated with oral administration of large quantities of diphosphonates.

BACKGROUND ART

U.S. Pat. 3,683,080, issued Aug. 8, 1972, to Francis, discloses compositions comprising polyphosphonates, in particular diphosphonates, and their use in inhibiting anomalous deposition and mobilization of calcium phosphate in animal tissue.

Japanese Pat. 80-98,193, issued July 25, 1980, to Nissan Kygaku Kagyo K.K. discloses pyridyl ethane diphosphonic acid, S-(pyridyl)-thiomethane diphosphonic acid, and the derivatives with halogen or alkyl group substitution on the pyridyl ring. These compounds are used as post-emergence herbicides.

Japanese Pat. 80-98,105, issued July 25, 1980, to Nissan Chemical Industries, discloses N-(3-pyridyl)-aminomethane diphosphonic acid, and the derivatives with halogen or alkyl group substitution on the pyridyl ring, for use as herbicides. Various N-(pyridyl)-aminomethane diphosphonates are also disclosed in West Ger. Pat. 2,831,578, issued February 1, 1979 to Fumio, for use as herbicides.

European Pat. Application 100,718 (Sanofi SA), published Feb. 15, 1984, discloses various alkyl diphosphonates which are ω-substituted by a sulfide attached to a 5- or 6-membered nitrogen- or sulfur-containing heterocycle. These compounds are used as anti-inflammatory and anti-rheumatic drugs.

European Pat. Application 151.072 (Sanofi), published Aug. 7, 1985, discloses various alkyl diphosphonates which are ω-substituted by an amino or substituted amino and by an alkyl sulphide attached to a 5- or 6-membered nitrogen- or sulfur-containing heterocycle. These compounds are used as anti-inflammatory and anti-rheumatic drugs.

British Pat. Application 2,004,888, published April 11, 1979, discloses N-(3-methyl-2-picolyl)-aminomethane and related compounds for use in herbicidal compositions.

W. Ploger et al., Z. Anorg. Allg. Chem., 389, 119 (1972), discloses the synthesis of N-(4-pyridyl)-aminomethane diphosphonic acid. No properties or utility of the compound are disclosed.

SUMMARY OF THE INVENTION

It is an object of this invention to provide an improved method for treating non-inflammatory diseases characterized by abnormal calcium and phosphate metabolism with high potency compositions.

The present invention relates to methods of treating non-inflammatory diseases characterized by abnormal calcium and phosphate metabolism comprising administering to a human or animal in need of such treatment a safe and effective amount of pharmaceutical compositions comprising from about 0.1 mg P to about 600 mg P of a geminal diphosphonic acid compound, or its pharmaceutically-acceptable salt or ester, in which the diphosphonic acid-containing carbon is linked via a chain of length from 1 to about 5 atoms, to a 6-membered aromatic ring containing one or more nitrogen atoms with the parts of said compound being comprised as follows:

(a) said ring may be unsubstituted or substituted with one or more substituents selected from the group consisting of substituted and unsubstituted alkyl (saturated or unsaturated) having from 1 to about 6 carbon atoms, substituted and unsubstituted aryl, substituted and unsubstituted benzyl, hydroxy, halogen, carbonyl, alkoxy, nitro, amido, amino, substituted amino, carboxylate, and combinations thereof;

(b) said linking chain may be a sulfur atom or sulfur-containing chain with said chain being unsubstituted or substituted on any carbon atoms, independently, with one or more substituted or unsubstituted, saturated or unsaturated alkyl having from 1 to about 4 carbon atoms;

(c) said diphosphonate-containing carbon may be unsubstituted or substituted with substituted or unsubstituted alkyl (saturated or unsaturated) having from 1 to about 6 carbon atoms, substituted or unsubstituted aryl, substituted or unsubstituted benzyl amino substituted amino, amido, hydroxy, alkoxy, halogen or carboxylate, except where said diphosphonate-containing carbon is directly bonded to a sulfur atom in the linking chain, then the substituents may be substituted or unsubstituted, saturated or unsaturated alkyl having from 1 to about 6 carbon atoms, substituted or unsubstituted aryl, or substituted or unsubstituted benzyl.

DETAILED DESCRIPTION OF THE INVENTION

This invention relates to methods of treating humans or animals with pharmaceutical compositions, preferably in unit dosage form, comprising a pharmaceutical carrier and a safe and effective amount of geminal diphosphonic acid compounds, or their pharmaceutically-acceptable salts and esters, in which the diphosphonic acid-containing carbon is linked to a 6-membered aromatic ring containing one or more nitrogen atoms. Preferred rings are pyridine, pyridazine, pyrimidine, and pyrazine. Most preferred are pyrimidine, and especially pyridine. The rings may be unsubstituted or substituted with one or more substituents selected from the group consisting of substituted and unsubstituted alkyl (saturated or unsaturated) having from 1 to about 6 carbon atoms, substituted and unsubstituted aryl (e.g., phenyl and naphthyl), substituted and unsubstituted benzyl, hydroxy, halogen, carbonyl (e.g., —CHO and —COCH$_3$), alkoxy (e.g., methoxy and ethoxy), nitro, amido (e.g., —NHCOCH$_3$), amino, substituted amino (e.g., dimethylamino, methylamino, and diethylamino), carboxylate (e.g., —OCOCH$_3$), and combinations thereof. The rings may be fused with other rings, e.g., benzene fused with pyridine (e.g., quinoline), and cyclohexane fused with pyridine (e.g., 5,6,7,8-tetrahydroquinoline). Additional substituents could be substituted or unsubstituted sulfide, sulfoxide, sulfate, or sulfone.

The linkage from the diphosphonic acid-containing carbon to the ring is by a chain of length of from 1 to about 5 atoms. The chain may be a sulfur atom or sulfur-containing chain. The carbon atoms in the chains may, independently, be unsubstituted or substituted with one or two substituted or unsubstituted alkyl (saturated or unsaturated) having from 1 to about 4 carbon atoms (methyl and ethyl being preferred). Unsubstituted carbon atoms in the chain are preferred. Also preferred is a chain of one sulfur atom.

The carbon atom which has the phosphonate groups attached to it may be unsubstituted (i.e., a hydrogen atom), or substituted with amino, substituted amino, amido, hydroxy, alkoxy, halogen, carboxylate, substituted or unsubstituted alkyl (saturated or unsaturated) having from 1 to about 6 carbon atoms, substituted or unsubstituted aryl, or substituted or unsubstituted benzyl. For the compounds in which the phosphonate-containing carbon is linked to the ring via a sulfur-containing chain, and that sulfur atom is bonded directly to the phosphonate containing carbon, then the substituent on the phosphonate-containing carbon may be substituted or unsubstituted alkyl (saturated or unsaturated) having from 1 to about 6 carbon atoms, substituted or unsubstituted aryl, or substituted or unsubstituted benzyl.

Thus, diphosphonic acid compounds to be used in the methods of the present invention have the structure:

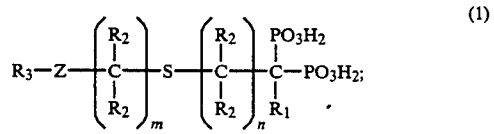

(1)

wherein m+n is an integer from 0 to about 5, with m+n=0 or 1 preferred; Z is a ring selected from the group consisting of pyridine, pyridazone, pyrimidine, and pyrazine, with preferred being pyrimidine, and especially pyridine; $R_1$ is hydrogen, substituted or unsubstituted amino, amido, hydroxy, alkoxy, halogen, carboxylate, substituted or unsubstituted alkyl (saturated or unsaturated) having from 1 to about 6 carbon atoms, substituted or unsubstituted aryl, or substituted or unsubstituted benzyl, except that when n=0 then $R_1$ is hydrogen, substituted or unsubstituted alkyl (saturated or unsaturated) having from 1 to about 6 carbon atoms, substituted or unsubstituted aryl, or substituted or unsubstituted benzyl, with $R_1$ being hydrogen, methyl, fluoro, chloro, amino, or hydroxy preferred; each $R_2$ is, independently, hydrogen, or substituted or unsubstituted alkyl (saturated or unsaturated) having from 1 to about 4 carbon atoms, with $R_2$ being hydrogen preferred; $R_3$ is one or more substituents selected from the group consisting of hydrogen, substituted or unsubstituted alkyl (saturated or unsaturated) having from 1 to about 6 carbon atoms, substituted and unsubstituted aryl, substituted and unsubstituted benzyl, hydroxy, halogen, carbonyl, alkoxy, nitro, amido, amino, substituted amino, carboxylate, and combinations thereof, with preferred being hydrogen, methyl, amino, chloro, methoxy, nitro, hydroxy and combinations thereof; and pharmaceutically-acceptable salts and esters of these compounds. Finally, for any of the $R_1$, $R_2$, or $R_3$ substituents which are themselves substituted, the substitution on these substituents may be any one or more of the above substituents, preferred being methyl, ethyl, amino, chloro, nitro, methoxy, hydroxy, acetamido, and acetate.

Generally preferred diphosphonic acid compounds, and their pharmaceutically acceptable salts and esters, to be included in the pharmaceutical compositions of the present invention are of the structure:

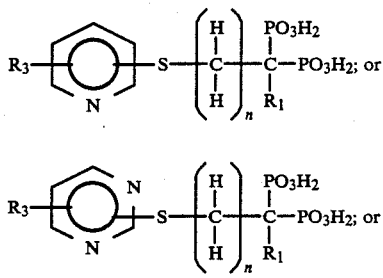

$$R_3 \text{—} \underset{N}{\bigcirc} \text{—} S \text{—} \left( \underset{\underset{H}{|}}{\overset{\overset{H}{|}}{C}} \right)_n \underset{R_1}{\overset{PO_3H_2}{|}} \text{—} C \text{—} PO_3H_2; \text{ or} \qquad (2)$$

$$R_3 \text{—} \underset{N}{\bigcirc}^{N} \text{—} S \text{—} \left( \underset{\underset{H}{|}}{\overset{\overset{H}{|}}{C}} \right)_n \underset{R_1}{\overset{PO_3H_2}{|}} \text{—} C \text{—} PO_3H_2; \text{ or} \qquad (3)$$

wherein for the two preceding structures n=0 or 1; R₁ is hydrogen, methyl, fluoro, chloro, amino, or hydroxy when n=1, and R₁ is hydrogen or methyl when n=0; R₃ is one or more substituents selected from the group consisting of hydrogen, methyl, amino, chloro, methoxy, nitro, hydroxy, and combinations thereof.

Specific examples of preferred compounds which may be utilized in methods of the present invention include:

S-(2-pyridyl)thiomethane diphosphonic acid
S-(3-pyridyl)thiomethane diphosphonic acid
S-(4-pyridyl)thiomethane diphosphonic acid
S-(2-pyrimidyl)thiomethane diphosphonic acid
S-[2-(3- or 4- or 5- or 6-methylpyridyl)]thiomethane diphosphonic acid
S-[3-(2- or 4- or 5- or 6-methylpyridyl)]thiomethane diphosphonic acid
S-[4-(2- or 3-methylpyridyl)]thiomethane diphosphonic acid and pharmaceutically-acceptable salts and esters thereof.

The diphosphonate compounds to be used in the methods of the present invention can be made using the synthetic methods disclosed in European Pat. Application 100,718 (Sanofi, SA, published Feb. 15, 1984), the disclosure of which is incorporated herein by reference. The thiomethane diphosphonic acid compounds are best prepared as follows:

EXAMPLE I

S-(2-pyridyl)thiomethane diphosphonic acid

To a suspension of potassium hydride (20 mmoles) at 5° C. suspended in 50 ml dry toluene under a nitrogen atmosphere, tetraisopropylmethane diphosphonate (20 mmoles) was added dropwise to form solution A. A solution of 2,2' dipyridyl disulfide (20 mmoles dissolved in 50 ml dry toluene) was added rapidly to solution A. The reaction mixture was stirred at room temperature for four hours. The reaction mixture was filtered and the solvent evaporated. The crude reaction mixture was chromatographed on silica gel, eluting with a 1:1 mixture of acetone and hexane. A pure fraction containing 3.2 g of tetraisopropyl S-(2-pyridyl)thiomethane diphosphonate was obtained. This ester was hydrolyzed by refluxing in 3N hydrochloric acid overnight. S-(2-pyridyl)thiomethane diphosphonic acid was obtained by evaporating the aqueous hydrochloric acid solution to dryness and recrystallizing the solid from water and ethanol.

EXAMPLE II

S-(2-picolyl)thiomethane diphosphonic acid

To a suspension of potassium hydride (20 mmoles) at 5° C. suspended in 50 ml dry toluene under a nitrogen atmosphere, tetraisopropylmethane diphosphonate (20 mmoles) was added dropwise to form solution A. A solution of S,S'-(α-2-picolyl)disulfide (20 mmoles dissolved in 50 ml dry toluene) was added rapidly to solution A. The reaction mixture was stirred at room temperature for four hours. The reaction mixture was filtered and the solvent evaporated. The crude reaction mixture was chromatographed on silica gel, eluting with a 1:1 mixture of acetone and hexane. A pure fraction containing 3.2 g of tetraisopropyl S-(2-picolyl)thiomethane diphosphonate was obtained. This ester was hydrolyzed by refluxing in 3N hydrochloric acid overnight. S-(2-picolyl)thiomethane diphosphonic acid was obtained by evaporating the aqueous hydrochloric acid solution to dryness and recrystallizing the solid from water and ethanol.

EXAMPLE III

S-(2-pyrimidyl)-2-thioethane-1,1-diphosphonic acid

To a tetrahydrofuran solution of 10 mmoles 2-mercaptopyrimidine (1.12 g) and 10 mmoles tetraethyulvinyldiphosphonate (3.0 g) cooled to 5° C. is added 10 drops of a 40% solution of benzyltrimethylammonium hydroxide in methanol. The mixture is stirred at room temperature overnight. The reaction solution is evaporated to dryness and the crude product chromatographed on silica gel using a 1:1 acetone/hexane solvent system. The resulting pure tetraethyl S-(2-pyrimidyl)-2-thioethane-1,1-diphosphonate is hydrolyzed by refluxing in 6N hydrochloric acid overnight. After evaporation of the hydrochloric acid solution the S-(2-pyrimidyl)-2-thioethane-1,1-diphosphonic acid is recrystallized from boiling water.

By "pharmaceutically-acceptable salts and esters" as used herein is meant hydrolyzable esters and salts of the diphosphonate compounds which have the same general pharmacological properties as the acid form from which they are derived, and which are acceptable from a toxicity viewpoint. Pharmaceutically-acceptable salts include alkali metal (sodium and potassium), alkaline earth metal (calcium and magnesium), non-toxic heavy metal (stannous and indium), and ammonium and low molecular weight substituted ammonium (mono-, di- and triethanolamine) salts. Preferred compounds are the sodium, potassium, and ammonium salts.

By "pharmaceutical carrier" as used herein is meant one or more compatible solid or liquid filler diluents or encapsulating substances. By "compatible" as used herein is meant that the components of the composition are capable of being commingled without interacting in a manner which would substantially decrease the pharmaceutical efficacy of the total composition under ordinary use situations.

Some examples of substances which can serve as pharmaceutical carrier are sugars such as lactose, glucose and sucrose; starches such as corn starch and potato starch; cellulose and its derivatives, such as sodium carboxymethylcellulose, ethylcellulose, cellulose acetate; powdered tragacanth; malt; gelatin; talc; stearic acid; magnesium stearate; calcium sulfate; vegetable oils, such as peanut oil, cottonseed oil, sesame oil, olive oil, corn oil and oil of theobroma; polyols such as propylene glycol, glycerin, sorbitol, mannitol, and polyethylene glycol; agar; alginic acid; pyrogenfree water; isotonic saline; and phosphate buffer solutions, as well as other non-toxic compatible substances used in pharmaceutical formulations. Wetting agents and lubricants such as sodium lauryl sulfate, as well as coloring agents, flavoring agents, lubricants, excipients, tableting agents, stabilizers, anti-oxidants and preservatives, can also be present. Other compatible pharmaceutical additives and actives (e.g., vitamin D or vitamin D metabolites, and mineral supplements) may be included in the pharmaceutical compositions used in the methods of the present invention.

Some sulfur-containing compounds are prone to oxidation. For any diphosphonic acid compounds of the present invention which are prone to oxidation, it is preferred that an antioxidant be incorporated in pharmaceutical dosage forms useful in the present invention. Examples of such antioxidants include ascorbic acid, Vitamin E, BHA and BHT.

The choice of a pharmaceutical carrier to be used in conjunction with the diphosphonates used in the present invention is basically determined by t he way the diphosphonate is to be administered. If the compound is to be injected, the preferred pharmaceutical carrier is sterile, physiological saline, the pH of which has been adjusted to about 7.4. However, the preferred mode of administering the diphosphonates in the methods of the present invention is orally, and the preferred unit dosage form is therefore tablets, capsules and the like, comprising from about 1 mg P to about 600 mg P of the diphosphonic acid compounds described herein. Pharmaceutical carriers suitable for the preparation of unit dosage forms for oral administration are well known in the art. Their selection will depend on secondary considerations like taste, cost, and shelf stability, which are not critical for the purposes of the present invention, and can be made without difficulty by a person skilled in the art. The pharmaceutical carrier employed in conjunction with the diphosphonates used in the methods of the present invention is used at a concentration sufficient to provide a practical size to dosage relationship. Preferably, the pharmaceutical carrier comprises from about 0.01% to about 99.99% by weight of the total composition.

EXAMPLE IV

Capsules are prepared by conventional methods, comprised as follows:

| Ingredient | Mg per capsule |
|---|---|
| S—(2-pyridyl)thiomethane diphosphonate, monsodium salt | 100 (as mg P) |
| Starch | 55.60 |
| Sodium lauryl sulfate | 2.90 |

The above capsules administered orally twice daily for 6 months substantially reduce bone resorption in a patient weighing approximately 70 kilograms afflicted with osteoporosis. Similar results are obtained when the S(2-pyridyl)thiomethane diphosphonate, monosodium salt in the above-described capsules is replaced with
S-(3-pyridyl)thiomethane diphosphonic acid
S-(4-pyridyl)thiomethane diphosphonic acid
S-(2-pyrimidyl)thiomethane diphosphonic acid
S-[2-(3- or 4- or 5- or 6-methylpyridyl)]thiomethane diphosphonic acid
S-[3-(2- or 4- or 5- or 6-methylpyridyl)]thiomethane diphosphonic acid
S-[4-(2- or 3-methylpyridyl)]thiomethane diphosphonic acid
or the pharmaceutically-acceptable salts or esters thereof.

EXAMPLE V

Tablets are prepared by conventional methods, formulated as follows:

| Ingredient | Mg per tablet |
|---|---|
| S—[4-(5-methylpyridyl)]thiomethane diphosphonate, monosodium salt | 25.00 |
| Lactose | 40.00 |
| Starch | 2.50 |
| Magnesium stearate | 1.00 |

The above tablets administered orally twice daily for 6 months substantially reduce bone resorption in a patient weighing approximately 70 kilograms afflicted with osteoporosis. Similar results are obtained when the S-[4-(5-methylpyridyl)]thiomethane diphosphonate, monosodium salt in the above-described tablets is replaced with
S-(2-pyridyl)thiomethane diphosphonic acid
S-(3-pyridyl)thiomethane diphosphonic acid
S-(4-pyridyl)thiomethane diphosphonic acid
S-(2-pyrimidyl)thiomethane diphosphonic acid
S-[2-(3- or 4- or 5- or 6-methylpyridyl)]thiomethane diphosphonic acid
S-[3-(2- or 4- or 5- or 6-methylpyridyl)]thiomethane diphosphonic acid
S-[4-(2- or 3-methylpyridyl)]thiomethane diphosphonic acid
or the pharmaceutically-acceptable salts or esters thereof.

EXAMPLE VI

Injectable solutions are prepared by conventional methods using 1.0 m of physiological saline solution and 1 mg of S-(2-pyrimidyl)thiomethane diphosphonic acid, adjusted to pH=7.4.

One injection, one time daily for 4 days results in appreciable alleviation of hypercalcemia of malignancy in patients weighing approximately 70 kilograms. Similar results are obtained when the S-(2-pyrimidyl)thiomethane diphosphonic acid in the above-described treatment is replaced with
S-(2-pyridyl)thiomethane diphosphonic acid
S-(3-pyridyl)thiomethane diphosphonic acid
S-(4-pyridyl)thiomethane diphosphonic acid
S-[2-(3- or 4- or 5- or 6-methylpyridyl)]thiomethane diphosphonic acid
S-[3-(2- or 4- or 5- or 6-methylpyridyl)]thiomethane diphosphonic acid
S-[4-(2- or 3-methylpyridyl)]thiomethane diphosphonic acid
or pharmaceutically-acceptable salts or esters thereof.

EXAMPLE VII

Patients weighing approximately 70 kilograms who are clinically diagnosed as suffering from hypercalcemia of malignancy are administered 7 mg P of S-(3-pyridyl)thiomethane diphosphonic acid, or its pharmaceutically-acceptable salt or ester, by a 2½ hour intravenous infusion one time daily for 4 days. This treatment results in an appreciable alleviation of the hypercalcemia of malignancy. Similar results are obtained when the S-(3-pyridyl)thiomethane diphosphonic acid in the above-described treatment is replaced with S-(2-pyridyl)thiomethane diphosphonic acid
S-(4-pyridyl)thiomethane diphosphonic acid
S-(2-pyrimidyl)thiomethane diphosphonic acid
S-[2-(3- or 4- or 5- or 6-methylpyridyl)]thiomethane diphosphonic acid
S-[3(2- or 4- or 5- or 6-methylpyridyl)]thiomethane diphosphonic acid
S-[4-(2- or 3-methylpyridyl)]thiomethane diphosphonic acid or pharmaceutically-acceptable salts or esters thereof.

The method of the present invention are useful in the treatment of abnormal calcium and phosphate metabolism. Other diphosphonic acids and their pharmaceutically-acceptable salts have been proposed for use in the treatment and prophylaxis of such conditions. In particular, ethane-1-hydroxy-1,1-diphosphonic acid (EHDP), propane-3-amino-1-hydroxy-1,1-diphosphonic acid (APD), and dichloromethane diphosphonic acid ($Cl_2MDP$) have been the subject of considerable research efforts in this area.

However, the compositions of the present invention are frequently more biologically potent in inhibiting bone resorption than the art-disclosed diphosphonates. In particular, it has been surprisingly found that the bone resorption inhibition potency of the compounds of the present invention is greater than that of corresponding compounds where the Z-ring (see chemical structure (1) hereinabove) does not contain one or more nitrogen atoms. Thus, the methods of the present invention may provide one or more of the following advantages over the art-disclosed diphosphonates of (1) being more potent in inhibiting bone resorption; (2) possessing less potential for inhibition of bone mineralization, since mineralization inhibition is believed to be predominantly a mass related physico-chemical effect; (3) having generally a wider margin of safety (i.e., wider dosing interval between the lowest effective antiresorptive dose and the lowest dose producing mineralization inhibition); (4) allowing lower oral dosages to be administered, thereby avoiding the gastro-intestinal discomfort (like diarrhea) sometimes associated with higher dosages of diphosphonates; and (5) having potential for flexibility of dosing methods.

The present invention is a method for treating or preventing non-inflammatory diseases characterized by abnormal calcium and phosphate metabolism, in particular those which are characterized by abnormal bone metabolism, in persons at risk to such disease, comprising the step of administering to persons in need of such treatment a safe and effective amount of a diphosphonic acid-containing composition.

The preferred mode of administration is oral, but other modes of administration include, without limitation, transdermal, mucosal, sublingual, intramuscular, intravenous, intraperitoneal, and subcutaneous administration, as well as topical application.

By "abnormal calcium and phosphate metabolism" as used herein is meant (1) conditions which are characterized by anomalous mobilization of calcium and phosphate leading to general or specific bone loss, or excessively high calcium and phosphate levels in the fluids of the body; and (2) conditions which cause or result from deposition of calcium and phosphate anomalously in the body. The first category includes, but is not limited to, osteoporosis, Pagets disease, hyperparathyroidism, hypercalcemia of malignancy, and osteolytic bone metastases. The second category includes, but is not limited to, myositis ossificans progressiva and calcinosis universalis.

By "person at risk", or "person in need of such treatment", as used herein is meant any human or lower animal which suffers a significant risk of abnormal calcium and phosphate metabolism if left untreated, and any human or lower animal diagnosed as being afflicted with abnormal calcium and phosphate metabolism. For example, postmenopausal women; persons undergoing certain steroid therapy; persons on certain anti-convulsant drugs; persons diagnosed as having Paget's disease, hyperparathyroidism, hypercalcemia of malignancy, or osteolytic bone metastases; persons diagnosed as suffering from one or more of the various forms of osteoporosis; persons belonging to a population group known to have a significantly higher than average chance of developing osteoporosis, e.g., postmenopausal women, men over age 65, and persons being treated with drugs known to cause osteoporosis as a side effect; and persons diagnosed as suffering from myositis ossificans progressiva or calcinosis universalis.

By "human or lower animal afflicted with or at risk to osteoporosis" as used herein is meant a subject diagnosed as suffering from one or more of the various forms of osteoporosis, or a subject belonging to a group known to have a significantly higher than average chance of developing osteoporosis, e.g., postmenopausal women, men over the age of 65, and persons being treated with drugs known to cause osteoporosis as a side effect (such as adrenocorticoid).

By "safe and effective amount" as used herein is meant an amount of a compound or composition high enough to significantly positively modify the condition to be treated, but low enough to avoid serious side effects (at a reasonable benefit/risk ratio), within the scope of sound medical judgment. The safe and effective amount of diphosphonates will vary with the particular condition being treated, the age and physical condition of the patient being treated, the severity of the condition, the duration of treatment, the nature of concurrent therapy, and the specific diphosphonate employed. However, single dosages can range from about 0.1 mg P to about 3500 mg P, or from about 0.01 mg P/kg of body weight to about 500 mg P/kg of body weight. Preferred single dosages are from about 1 mg P to about 600 mg P, or from about 0.1 mg to about 50 mg P/kg of body weight. Up to about four single dosages per day may be administered. Daily dosages greater than about 2000 mg P/kg are not required to produce the desired effect and may produce undesirable side effects. The higher dosages within this range are, of course, required in the case of oral administration because of limited absorption.

Thyroparathyroidectomized (TPTX) Rat Model

The compounds were evaluated for in vivo bone resorption inhibition potency by an animal model system known as the thyroparathyroidectomized (TPTC) rat model. The general principles of this model system are disclosed in Russell et al., Calcif. Tissue Research, 6, 183–186 (1970), and in Muhlbauer and Fleisch, Mineral Electrolyate Metabl., 5, 296–303 (1981), the disclosures of which are incorporated herein by reference. The basic biochemical concept of the TPTX system is inhibition of the parathyroid hormone (PTH) - induced rise in serum and ionized calcium levels by the respective bone active polyphosphonates.

Materials and Methods

Materials

Low calcium and low phosphorous diets used were prepared by Teklad ®Test Diets (Harlan Industries, Madison, Wisconsin 53711; Order #TD82195) in a pellet form of approximately 0.18% calcium and 0.22% phosphorous. The diets contained all the essential vitamins and minerals required for the rat, with the exception of calcium and phosphorous. The calcium and phosphorous levels of the pellets were verified analytically (Proctor & Gamble Co., Miami Valley Laboratories, Cincinnati, Ohio).

PTH was acquired as a powdered bovine extract (Sigma Chemical Co., P. O. Box 14508, St. Louis, Missouri, order #P-0892, Lot #72F-9650) at an activity of 138 USP units per mg. PTH was prepared in 0.9% saline such that the final concentration was 100 U.S.P./ml. All solutions were filtered through a #4 Whatman Filter Paper and refiltered through a0.45 μm Metricel ® filter.

Dose Solutions and Dosing Procedure

All solutions of compounds to be tested for bone resorption inhibition potency were prepared for subcutaneous injection in 0.9% normal saline and adjusted to pH 7.4 using NaOH and/or HCl. Dose solution calculation was made by considering the mass of powder (based on molecular weight, hydration) of the active material in mg/kg (body weight) that corresponds to mg P/kg. Concentrations were based on dosing 0.2 ml/100 grams of body weight. Initially, all compounds were administered at 0.01, 0.1, and 1.0 mg P/kg/day for 4 days. Where necessary the test was repeated, whereby the animals were administered with 0.5 LED in order to refine the determination of LED. Adjustments in dosage based on changes in body weight were made on a daily basis.

Animals

In this study 50 male Wistar rats weighing approximately 150–160 grams were thyroparathyroidectomized surgically by the breeder (Charles River Breeding Laboratories). All rats were double housed on arrival in suspended cages with Purina Laboratory Rodent Chow and tap water ad libitum. After acclimation to the laboratory environment for 3–5 days, the rats were placed on a low calcium, low phosphorous (0.18%/0.22%) diet (Teklad ®) and given 2% (W/V) calcium gluconate supplemented deionized water via water bottles.

Method

On day four of low-calcium diet all rats were anesthetized with Ketaset ®(Ketamine Hydrochloride, 100 mg/ml, Bristol Myers), 0.10 ml/100 grams of body weight, weighed and then bled from the retro-orbital venous plexus for serum total calcium analysis using Flame Atomic Absorption (FAA). All rats weighing less than 180 grams were eliminated from the study. Animals were then randomized statistically such that the mean total serum calcium for each group was the same. Only rats deemed hypocalcemic (total serum calcium ≦8.0 mg/dl) were placed in study groups comprising six animals per group.

Treatments with the various experimental compounds commenced on day 6 and lasted through day 9 of the study (at 1:00 P.M. each day). Dose solutions were prepared to be given at a constant rate of 0.2 ml/100 grams of body weight subcutaneously in the ventral skin flap where the hind leg meets the torso. All rats were weighed and dose daily. A 25 gauge ⅝" needle was used to administer drug, alternating dose sites daily. On day 8, animals were changed to deionized, distilled water via water bottles. On day 9 all rats were fasted in the afternoon at approximately 4:00 P.M. On day 10 of study no treatment was given. In the morning a 600 μl sample of whole blood was collected from each rat in Microtainer (B-D#5060) serum separater tubes for serum total calcium (FAA). Two 125 μl samples of heparinized whole blood were also collected to be used for ionized calcium analysis. Immediately following blood collection all rats were weighed and injected with bovine parathyroid hormone subcutaneously at a rate of 75 USP (filtered) per 100 grams of body weight. Blood sampling for total and ionized calcium was repeated three and one-half hours post-PTH injection.

All pre- and post-PTH total and ionized calciums were statistically analyzed for significance compared to PTH alone (control) using Students t-test, analysis of variance, and their non-parametric equivalents. The post minus pre-change and % change were also determined on calcium levels and pre-drug vs post-drug body weights.

The physiological effect of the PTH challenge is a rise in serum calcium level, with peak activity observed at three and one-half hours. Since the hormonal and dietary controls of calcium metabolism are minimized in the TPTX model, an observed increase in serum calcium level is presumably the result of resorption of bone material. Since polyphosphonates tend to inhibit resorption of bone materials, the animals pretreated with polyphosphonate showed a rise in serum calcium level after PTH challenge which was less than that found in control animals which had been treated with saline vehicle instead. The lowest dose at which the polyphosphonate is capable of inhibiting bone resorption, as evidenced by a decreased rise in serum calcium upon PTH challenge, is a measure of the bone resorption inhibition potency of the polyphosphonate. The LED values of the bone resorption inhibition potency of representative compounds as determined by the TPTX rat model are presented in Table I.

TABLE I

Lowest Effective (Antiresorptive) Dose

| Diphosphonate Compound | TPTX LED (mg P/kg) |
|---|---|
| EHDP | 1.0 |
| Cl$_2$MDP | 1.0 |
| APD | 0.1 |
| Phenylthiomethane DP | 1.0 |
| S—(2-pyridyl)thiomethane DP* | 0.1 |
| S—(4-pyridyl)thiomethane DP* | 0.1 |

DP = diphosphonic acid or a sodium salt thereof
EHDP = ethane-1-hydroxy-1,1-DP
Cl$_2$MDP = dichloromethane DP
APD = 3-aminopropane-1-hydroxy-1,1-DP
* = Compounds included in methods of the present invention

What is claimed is:

1. A method for treating a non-inflammatory disease characterized by abnormal calcium and phosphate metabolism selected from the group consisting of osteoporosis, Paget's disease, hyperparathyroidism, hypercalcemia of malignancy, osteolytic bone metastases, myositis ossificans progressiva and calcinosis universalis, comprising administering to a human or animal in need of such treatment a safe and effective amount of a pharmaceutical composition comprising from about 0.1 mg P to about 600 mg P of a geminal diphosphonic acid compound, or a pharmaceutically-acceptable salt or ester thereof, having the structure:

$$R_3-Z-\left(\begin{array}{c}R_2\\|\\C\\|\\R_2\end{array}\right)_m-S-\left(\begin{array}{c}R_2\\|\\C\\|\\R_2\end{array}\right)_n\begin{array}{c}PO_3H_2\\|\\C-PO_3H_2;\\|\\R_1\end{array}$$

wherein Z is a 6-membered aromatic ring containing one or more nitrogen atoms; m +n is an integer from 0 to about 5; $R_1$ is hydrogen, substituted or unsubstituted amino, amido, hydroxy, alkoxy, halogen, carboxylate, substituted or unsubstituted, saturated or unsaturated alkyl having from 1 to about 6 carbon atoms, substituted or unsubstituted aryl, or substituted or unsubstituted benzyl, except that when n =0, then $R_1$ is hydrogen, substituted or unsubstituted, saturated or unsaturated alkyl having from 1 to about 6 carbon atoms, substituted or unsubstituted aryl, or substituted or unsubstituted benzyl; $R_2$ is hydrogen, or substituted or unsubstituted, saturated or unsaturated alkyl having from 1 to about 4 carbon atoms; $R_3$ is one or more substituents selected from the group consisting of hydrogen, substituted and unsubstituted, saturated or unsaturated alkyl having from 1 to about 6 carbon atoms, substituted and unsubstituted aryl, substituted and unsubstituted benzyl, hydroxy, halogen, carbonyl, alkoxy, nitro, amido, amino, substituted amino, carboxylate, and combinations thereof.

2. The method for treating diseases according to claim 1, wherein Z is selected from the group consisting of pyridine, pyridazine, pyrimidine and pyrazine.

3. The method for treating diseases according to claim 2, wherein Z is pyridine.

4. The method for treating diseases according to claim 2, wherein Z is pyrimidine.

5. The method for treating diseases according to claim 2, wherein m+n=1.

6. The method for treating diseases according to claim 2, wherein m+n=2.

7. The method for treating diseases according to claim 2, wherein m+n=0.

8. The method for treating diseases according to claim 3, wherein said pharmaceutical composition comprises from about 0.1 mg P to about 600 mg P of a geminal diphosphonic acid compound, or a pharmaceutically-acceptable salt or ester thereof, having the structure:

$$R_3-\underset{N}{\underset{|}{\bigcirc}}-S-(CH_2)_n-\underset{R_1}{\overset{PO_3H_2}{\underset{|}{C}}}-PO_3H_2$$

wherein n=0 or 1; $R_1$ is hydrogen, methyl, fluoro, chloro, amino, or hydroxy when n=1, and $R_1$ is hydrogen or methyl when n=0; $R_3$ is one or more substituents selected from the group consisting of hydrogen, methyl, amino, chloro, methoxy, nitro, hydroxy, and combinations thereof.

9. The method of treating diseases according to claim 8 wherein n=0, $R_1$ is hydrogen, and $R_3$ is hydrogen or methyl.

10. The method of treating diseases according to claim 4, wherein said pharmaceutical composition comprises from about 0.1 mg P to about 600 mg P of a geminal diphosphonic acid compound, or a pharmaceutically-acceptable salt or ester thereof, having the structure:

$$R_3-\underset{N}{\overset{N}{\bigcirc}}-S-(CH_2)_n-\underset{R_1}{\overset{PO_3H_2}{\underset{|}{C}}}-PO_3H_2$$

wherein n=0 or 1; $R_1$ is hydrogen, methyl, fluoro, chloro, amino, or hydroxy when n=1, and $R_1$ is hydrogen or methyl when n=0; $R_3$ is one or more substituents selected from the group consisting of hydrogen, methyl, amino, chloro, methoxy, nitro, hydroxy, and combinations thereof.

11. The method of treating diseases according to claim 2 wherein said pharmaceutical composition comprises from about 1 mg P to about 600 mg P of a geminal diphosphonic acid compound, or a pharmaceutically-acceptable salt or ester thereof, selected from the group consisting of S-(2-pyridyl)thiomethane diphosphonic acid
S-(3-pyridyl)thiomethane diphosphonic acid
S-(4-pyridyl)thiomethane diphosphonic acid
S-(2-pyrimidyl)thiomethane diphosphonic acid
S-[2-(3- or 4- or 5- or 6-methylpyridyl)]thiomethane diphosphonic acid
S-[3-(2- or 4- or 5- or 6-methylpyridyl)]thiomethane diphosphonic acid
S-[4-(2- or 3-methylpyridyl)]thiomethane diphosphonic acid and pharmaceutically-acceptable salts and esters thereof.

12. The method of treating diseases according to claim 11 wherein said pharmaceutical composition comprises from about 0.1 mg P to about 600 mg P of S-(2-pyridyl)thiomethane diphosphonic acid, or a pharmaceutically-acceptable salt or ester thereof.

13. The method of treating diseases according to claim 11 wherein said pharmaceutical composition comprises from about 0.1 mg P to about 600 mg P of S-(3-pyridyl)thiomethane diphosphonic acid, or a pharmaceutically-acceptable salt or ester thereof.

14. The method of treating diseases according to claim 11 wherein said pharmaceutical composition comprises from about 0.1 mg P to about 600 mg P of S-(4-pyridyl)thiomethane diphosphonic acid, or a pharmaceutically-acceptable salt or ester thereof.

15. The method of treating diseases according to claim 11 wherein said pharmaceutical composition comprises from about 0.1 mg P to about 600 mg P of S-(2-pyrimidyl)thiomethane diphosphonic acid, or a pharmaceutically-acceptable salt or ester thereof.

16. The method for treating diseases according to claim 8, wherein said disease is osteoporosis.

17. The method for treating diseases according to claim 9, wherein said disease is osteoporosis.

18. The method for treating diseases according to claim 10, wherein said disease is osteoporosis.

19. The method for treating diseases according to claim 11, wherein said disease is osteoporosis.

* * * * *